United States Patent [19]

Perregaard

[11] Patent Number: 4,855,307

[45] Date of Patent: Aug. 8, 1989

[54] ACETIC ACID ESTER OF HALOPERIDOL

[75] Inventor: Jens K. Perregaard, Olstykke, Denmark

[73] Assignee: H. Lundbeck A/S, Copenhagen, Denmark

[21] Appl. No.: 93,404

[22] Filed: Sep. 4, 1987

[30] Foreign Application Priority Data

Sep. 11, 1986 [GB] United Kingdom ............... 8621892

[51] Int. Cl.⁴ .................. A61K 31/435; C07D 211/52
[52] U.S. Cl. ..................................... 514/327; 546/218
[58] Field of Search ............... 546/217, 218; 514/327

[56] References Cited

U.S. PATENT DOCUMENTS 3,408,356  10/1968  Horovitz ........................... 546/217
4,070,473   1/1978  Hernestom et al. ............... 514/327

FOREIGN PATENT DOCUMENTS 1131534  7/1967  United Kingdom .

OTHER PUBLICATIONS

Chemical Abstracts: 97 60926U; E. Say et al., "Bioavailability and Clinical Effects of Two Different Concentrations of Haloperidoldecanoate", (1982).

Chemical Abstracts 94: 180676X, C. Niemegeers, "Parental Psychotropic Preparation with Long Term Action", (1981).

*Primary Examiner*—Richard L. Raymond
*Assistant Examiner*—Mark W. Russell
*Attorney, Agent, or Firm*—Gordon W. Hueschen

[57] ABSTRACT

The present invention relates to the novel acetic acid ester of 4-(4-(4-chlorophenyl)-4-hydroxy-1-piperidinyl)-1-(4-fluorophenyl)-1-butanone, as well as pharmaceutically acceptable acid addition salts thereof, a method of preparation, pharmaceutical compositions and a method of treating psychoses by administering said ester to an animal or human body.

8 Claims, No Drawings

ACETIC ACID ESTER OF HALOPERIDOL

BACKGROUND OF THE INVENTION

The compound 4-(4-(4-chlorophenyl)-4-hydroxy-1-piperidinyl)-1-(4-fluorophenyl)-1-butanone, known as haloperidol (INN), has for many years been a widely used neuroleptic in the treatment of severe psychotic conditions including schizophrenic disorders.

So far, haloperidol has been administered orally or in form of aqueous solutions for injection containing haloperidol and lactic acid. Moreover, a very long acting depot preparation consisting of the decanoic acid ester of haloperidol in sesame oil is known.

The aqueous solution for injection which is relatively short acting and used in the acute phase, has however in most cases very serious side effects at the site of injection in the form of necrosis of the muscle tissue.

Accordingly, there has been a need for short acting injectable preparations of haloperidol causing less damage of the muscle tissue.

SUMMARY OF THE INVENTION

It has now according to the present invention been found that by substituting the aqueous solutions of haloperidol with solutions in pharmaceutically acceptable oils of the so far unknown acetic acid ester of haloperidol, or a pharmaceutically acceptable acid addition salt thereof, practically no damage of muscle tissue occurred, at the same time as a reasonably rapid onset of antipsychotic effect was obtained, lasting for 2-7 days.

The compositions of the present invention are prepared by dissolving or suspending the acetic acid ester of haloperidol, or a pharmaceutically acceptable acid addition salt thereof, in a pharmaceutically acceptable oil under sterile conditions. The preferred oils are of vegetable origin such as peanut oil, sesame oil, cotton seed oil, corn oil, soybean oil, olive oil and most preferably light vegetable oil.

According to the method of the invention haloperidol is reacted with a reactive derivative of acetic acid in a solvent and isolated in the form of the free base or a pharmaceutically acceptable acid addition salt thereof.

As reactive derivatives of acetic acid may especially be mentioned the anhydride or an acetylhalide, preferably the chloride.

The solvent used in the reaction may advantageously be pyridine or an inert solvent containing an acid binding agent.

The reaction may preferably be carried out at elevated temperature such as reflux temperature.

This invention also includes pharmaceutically acceptable salts of the acetic acid ester of 4-(4-(4-chlorophenyl)-4-hydroxy-1-piperidinyl)-1-(4-fluorophenyl)-1-butanone formed with non-toxic organic or inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether, with the desired salt separating directly. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromo-theophylline. Examplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

The method of the invention shall in the following be illustrated with some examples which may not be construed as limiting for the scope of the invention:

EXAMPLE 1

4-(4-Acetoxy-4-(4-chlorophenyl)-1-piperidinyl)-1-(4-fluorophenyl)-1-butanone (Haloperidol-acetate)

4-(4-(4-Chlorophenyl)-4-hydroxy-1-piperidinyl)-1-(4-fluorophenyl)-1-butanone (20 g) and acetic acid anhydride (16 g) in 200 ml of dried pyridine (KOH pellets) were refluxed for 2 h. The mixture was poured into cold $H_2O$ (0° C.) (2 liters) and extracted with isopropylether (2×200 ml). The combined organic phases were dried ($MgSO_4$) and the solvent evaporated. The title compound was obtained after column chromatography on silica gel (eluent, ethyl acetate/dichloromethane/methanol, 1:1:1). Yield 10.6 g (48%). Mp 106°-110° C. (from isopropyl ether). The hydrochloride salt was precipitated from acetone. Mp 215° C. According to TLC analysis the content of Haloperidol was 0.5%.

The following examples of formulations illustrate the compositions of the present invention:

EXAMPLE 2

Haloperidol acetate: 5 grams
Thin vegetable oil BP(Viscoleo ®): ad 100 ml.

EXAMPLE 3

Haloperidol acetae: 2 grams
Sesame oil BP: ad 100 ml.

EXAMPLE 4

Haloperidol acetate: 3 grams
Thin vegetable oil BP: ad 100 ml.

EXAMPLE 5

Haloperidol acetate: 10 grams
Olive oil: ad 100 ml.

EXAMPLE 6

Haloperidol acetate: 5 grams
Sesame oil BP: ad 100 ml.

The solutions according to Examples 2–6 are made under sterile conditions and filled into suitable receptacles such as ampoules or vials, each containing 1–3 ml solution.

The compositions of the present invention are preferably administered in unit dosage form in ampoules or vials, the solution or suspension containing from about 1 mg to about 100 mg of active ingredient per ml of solution or suspension.

Some of the above compositions of Examples 2–6 were tested for their ability to protect dogs against vomiting caused by apomorphine. The test has been described by Janssen, P. A. J., Niemegeers, C. J. E. and K. H. L. Scheelekens, Arzneimittel-Forschung, 1965, 15, 1196–1201.

It was found that a good protection was achieved compared with corresponding injections of aqueous solutions of unesterified haloperidol.

The local toxicity at the injection site was tested in pigs. 2 ml of test solution were injected intramuscularly. Three days after injection the pigs were anaesthetized and killed by exsanguination. Macroscopic changes at the injection site were noted, and quantity of the damaged or depleted muscle tissue was determined by measurement of depletion of creatinphosphokinase (CK). Whereas the compositions of the present invention showed only slight depletion of CK in about 0.15-0.40 g of muscle tissue, and almost with none macroscopic findings, the corresponding test with a commercial 0.5% aqueous solution of haloperidol as the lactase showed depletion of CK in about 6 g of muscle tissue with pronounced macroscopic findings of necrotic muscle tissue sharply demarcated from surrounding healthy tissue.

Results upon administration of the neuroleptic compositions of the present invention to human beings have been very gratifying.

The invention also comprises a method for the alleviation, palliation, mitigation or inhibition of the manifestations of certain psychic abnormalities of animals by administering to a living animal body, including human beings, an adequate quantity of a composition according to the present invention. An adequate quantity would be from about 0.005 mg til about 1 mg per kilo of body weight in each injection dosis.

It is to be understood that the invention is not limited to the exact details of operation or exact compound or compositions shown and described, as obvious modifications and equivalents will be apparent to one skilled in the art.

I claim:

1. The acetic acid ester of 4-(4-(4-chlorophenyl)-4-hydroxy-1-piperidinyl)-1-(4-fluorophenyl)-butanone, or a pharmaceutically-acceptable acid addition salt thereof.

2. Compound of claim 1 being the acetic acid ester of 4-(4-(4-chlorphenyl)-4-hydroxy-1-piperidinyl)-1-(4-fluorophenyl)-butanone.

3. An injectable pharmaceutical composition containing as an active ingredient an effective amount of a compound of claim 1, and as a carrier a pharmaceutically-acceptable oil.

4. A pharmaceutical composition according to claim 3, wherein the active ingredient is the compound of claim 2.

5. A pharmaceutical composition according to claim 3, in unit dosage form wherein the active ingredient is present in an amount of from 1 mg to 100 mg per ml of solution or suspension.

6. A pharmaceutical composition according to claim 3, wherein the oil is sesame oil.

7. A pharmaceutical composition according to claim 3, wherein the oil is thin vegetable oil BP.

8. Method of treating psychoses comprising the step of administering parenterally to a subject in need thereof an antipsychotic amount of a compound of claim 1 or a pharmaceutical composition thereof containing said compound together with a pharmaceutically-acceptable oil carrier.

* * * * *